(12) United States Patent
Tickner et al.

(10) Patent No.: US 6,224,554 B1
(45) Date of Patent: May 1, 2001

(54) METHOD TO MEASURE AMBIENT FLUID PRESSURE

(75) Inventors: E. Glenn Tickner, Los Gatos; Stanley R. Conston, San Carlos, both of CA (US)

(73) Assignee: Point Biomedical Corporation, San Carlos, CA (US)

( * ) Notice: Subject to any disclaimer, the term of this patent is extended or adjusted under 35 U.S.C. 154(b) by 0 days.

(21) Appl. No.: 09/282,514

(22) Filed: Mar. 31, 1999

(51) Int. Cl.$^7$ ........................................... A61B 8/00
(52) U.S. Cl. ............................. 600/438; 600/458
(58) Field of Search ..................... 600/437, 438, 600/458; 73/1.85

(56) References Cited

U.S. PATENT DOCUMENTS

| | | | |
|---|---|---|---|
| 3,640,271 | 2/1972 | Horton | 128/2.05 |
| 4,265,251 | 5/1981 | Tickner | 128/660 |
| 4,483,345 | * 11/1984 | Miwa | 600/438 |
| 5,195,520 | 3/1993 | Schlief et al. | 128/660 |
| 5,447,161 | 9/1995 | Blazek et al. | 128/677 |
| 5,518,709 | * 5/1996 | Sutton et al. | 600/438 |
| 5,535,747 | * 7/1996 | Katakura | 600/438 |
| 5,694,937 | * 12/1997 | Kamiyama | 600/458 X |
| 5,735,281 | * 4/1998 | Rafter et al. | 600/458 |
| 5,743,266 | * 4/1998 | Levene et al. | 600/458 |
| 5,749,364 | 5/1998 | Sliwa Jr. et al. | 128/662 |
| 5,971,928 | * 10/1999 | Dodd et al. | 600/458 |

FOREIGN PATENT DOCUMENTS

WO98/32378   7/1998  (WO) .

OTHER PUBLICATIONS

Aakhus, MD., et al., "Noninvasive Computerized Assessment of Left Ventricular Performance and Systemic Hemodynamics by Study of Aortic Root Pressure and Flow Estimates in Healthy Men, and Men with Acute and Healed Myocardial Infarction", The Amer. J. Of Cardiology, vol. 72. Aug. 1, 1993, 260–267.

Bouakez et al., "On the effect of lung filtering and cardiac pressure on the standard properties of ultrasound contrast agent", Ultrasonics, 36, 703–708, 1998.

Currie et al., "Continuous Wave Deppler Dermination of Right Ventricular Pressure: A Simultaneous Doppler—Catheterization Study in 127 Patients," JACC vol. 6, No. 4, Oct/1985, 750–6.

Gersh et al., "Physical criteria for measurement of left ventricular pressure and its first derivative'", cardiovascular Res. 1971, 5, 32–40.

Hasegawa et al., "Acoustic radiation pressure acting on spherical and cylindrical shells", J. Acoust. Soc. Am. 93, 1, 1/93, 154–161.

Himelman M.D., et al., "Noninvasive Evaluation of Pulmonary Artery Pressure During Exercise by Saline–Enhanced Doppler Echocardiography in Chronic Pulmonary Disease", Circulation vol. 79, No.4, Apr. 1989, 863–869.

(List continued on next page.)

*Primary Examiner*—Francis J. Jaworski
(74) *Attorney, Agent, or Firm*—Fish & Richardson P.C.

(57) ABSTRACT

A method is provided for measuring real time ambient pressure at a region of interest in a fluid-filled body cavity by introducing into the cavity a composition of gas-containing microbubbles having a predetermined fragility threshold correlating to the rupture response of their capsules to the ambient fluid pressure and/or applied acoustic pressure. An ultrasonic signal is applied at the region of interest at a power level sufficient to destroy the microbubble population having a fragility threshold below the applied power level. The ultrasound backscatter response is detected from the population of intact and disintegrating microbubbles remaining at the region of interest and this backscatter signal is correlated to predetermined acoustic response properties to determine the ambient pressure at the region of interest.

43 Claims, 4 Drawing Sheets

AVERAGE ACOUSTIC DENSITOMETRY VALUE vs AMBIENT FLUID PRESSURE

EQUATION OF TRENDLINE
y = -0.1211x + 41.873
$R^2$ = 0.9603

OTHER PUBLICATIONS

Ishihara et al., "New Approach to Noninvasive Manometry Based on Pressure Dependent Resonant Shift of Elastic Microcapsules in Ultrasonic Frequency Characteristics", Pros. Of 8th symposium on Ultras. Elect. Tokyo 1987, Jap. J. Of Applied Physics, vol. 27, 1988, pp. 125–127.

Kyriakides et al., "Noninvasive determination of the left ventricular end–systolic pressure", Am.J.of Card.33, 1991, 267–274.

Laaban, M.D., et al., "Noninvasive Estiamtion of Systolic Pulmonary Artery Pressure Using Doppler Echocardiography in Patients with Chronic Obstructive Pulmonary Disease", Chest, 96, Dec. 1989, 1258–1262.

P.A.Lewin, "Acoustic pressure amplitude thresholds for rectified diffusion in gaseous microbubbles in biological tissue", J.Acoust.Soc.am. 69, 3, Mar. 1981, 846–852.

Neumann et al., "Accurate Noninvasive Estimation of Left Ventricular End–Diastolic Pressure: Comparison with Catheterization", J. of Amer. Soc. Of Echocardiography, vol. 11, No.2, 1998, 126–131.

W.L.Nyborg, "Radiation Pressure on a Small Rigid Sphere", The J. of the Acoustic. Soc. Of Amer., May 1967, 947–952.

Oesterle M.D., et al., "A New Method for Assessing Right–Sided Heart Pressure Using Encapsulated Microbubbles—A Preliminary Report", The Western J. Of Med., Oct. 1985, 463–468.

Serruys M.D. et al., "Intracoronary Pressure and Flow Velocity with Sensor–Tip Guidewires: A New Methodologic Approach for Assessment of Coronary Hemodynamics Before and After Coronary Interventions", The Amer. J.of Card.vol.71, May 20, 1993, 41D–53D.

Vuille M.D., et al., "Effect of Static Pressure on the Disappearance Rate of Specific Echocardiographic Contrast Agents", J.of the Amer.Soc.of Echocardiography Jul. 8,1994, 347–354.

Yosioka et al., "Acoustic Radiation Pressure on a Compressible Sphere", ACUSTICA vol. 5, 1955, 167–173.

Yosioka et al., "Acoustic Radiation Pressure on Bubbles and Their Logarithmic Decrement", ACUSTICA, vol.5, 1955, 173–178.

* cited by examiner

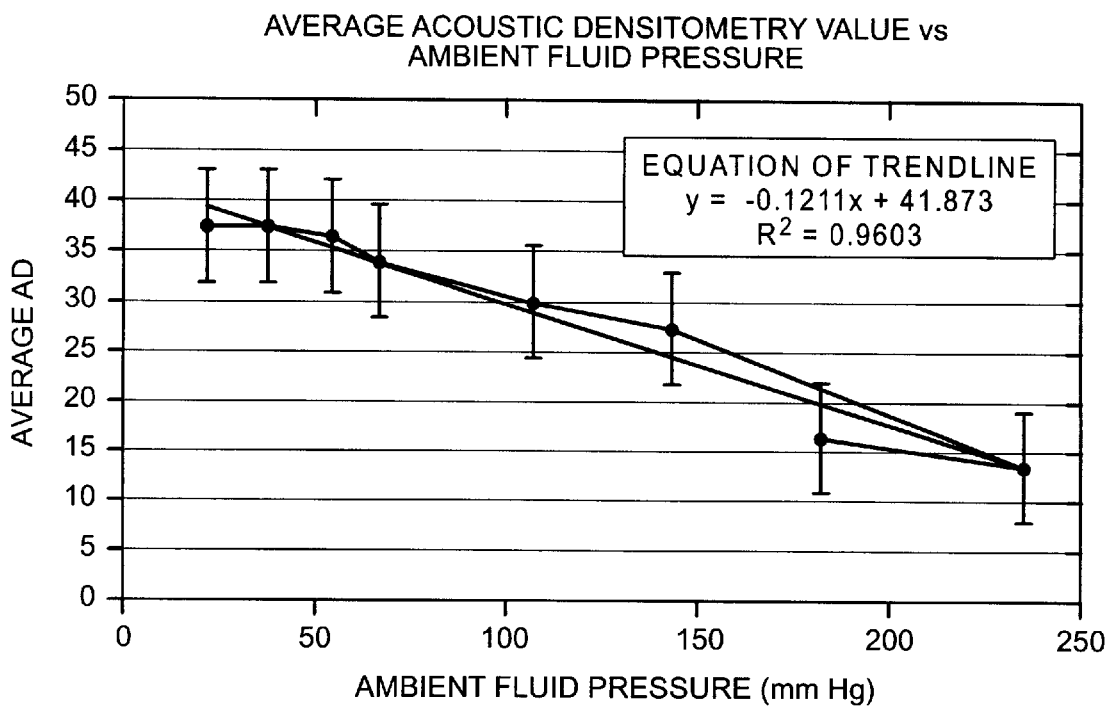
FIG._1
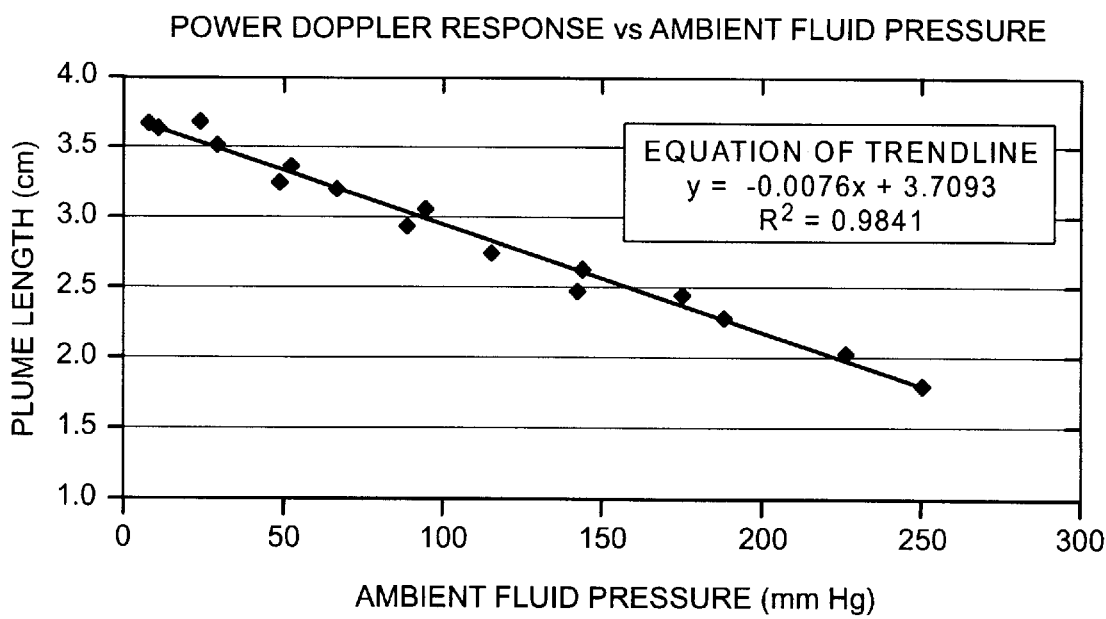
FIG._2

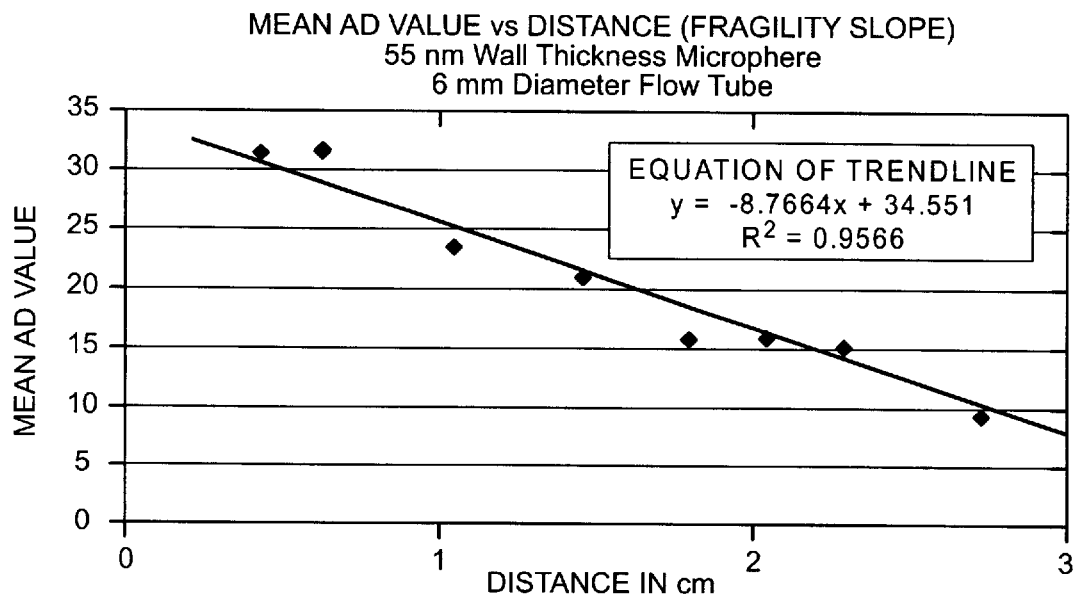
FIG._3
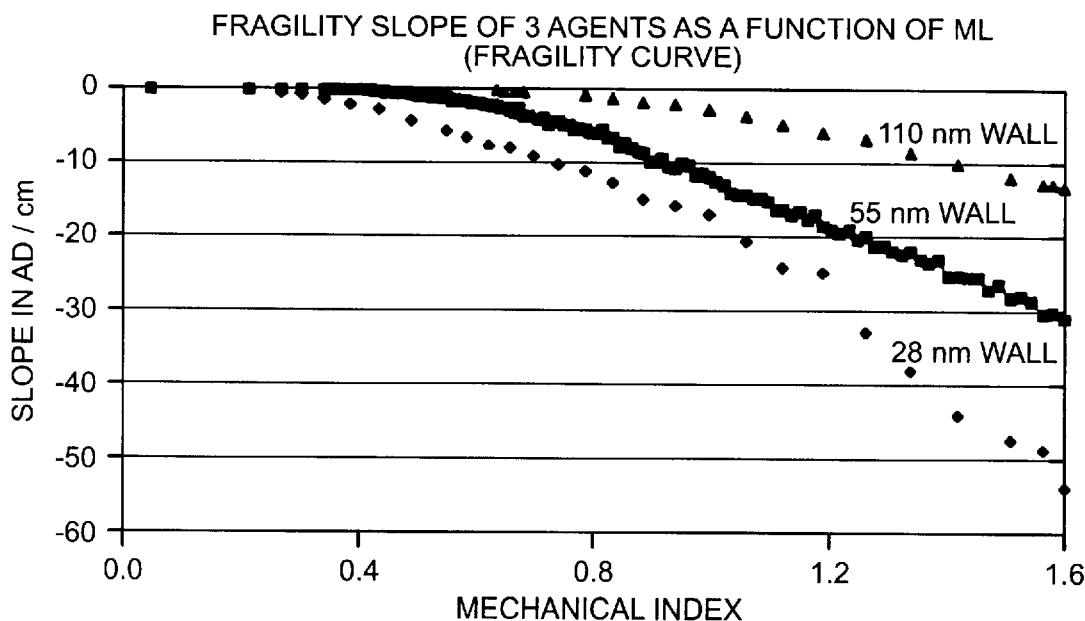
FIG._4

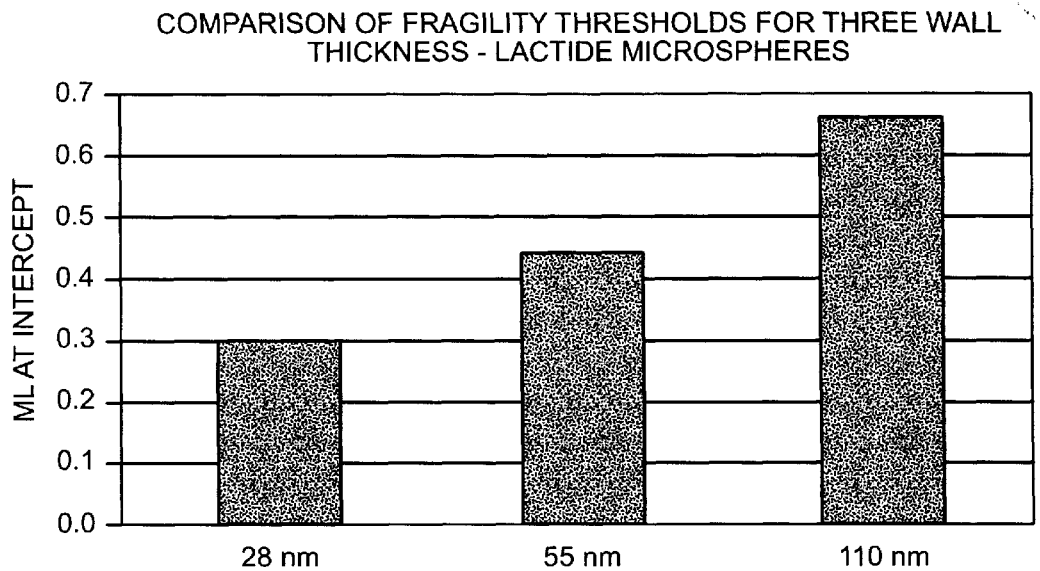
FIG._5
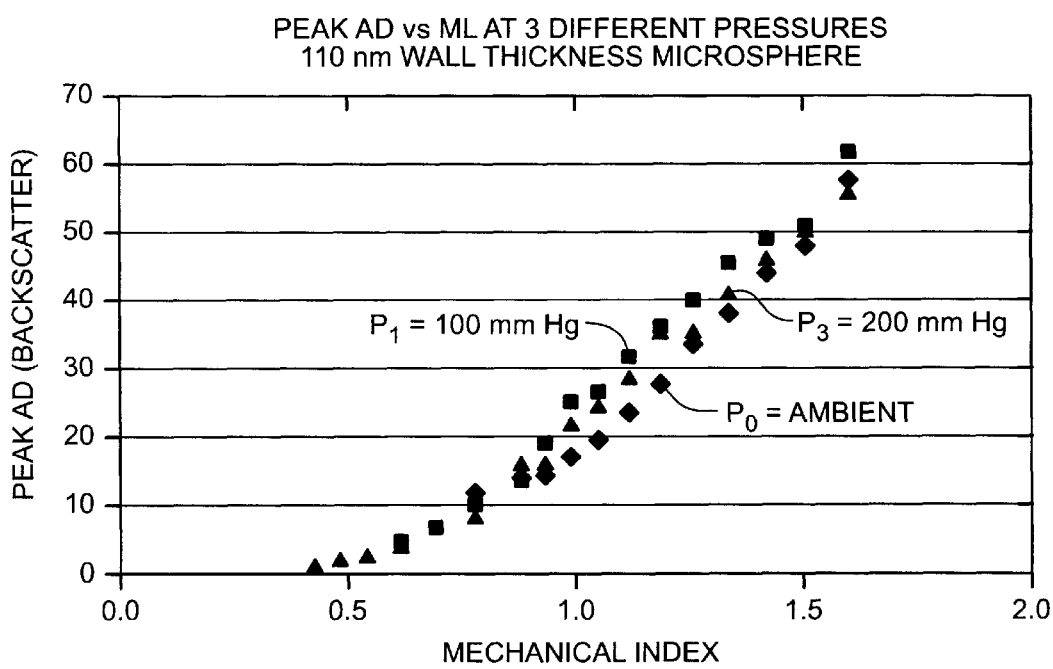
FIG._6

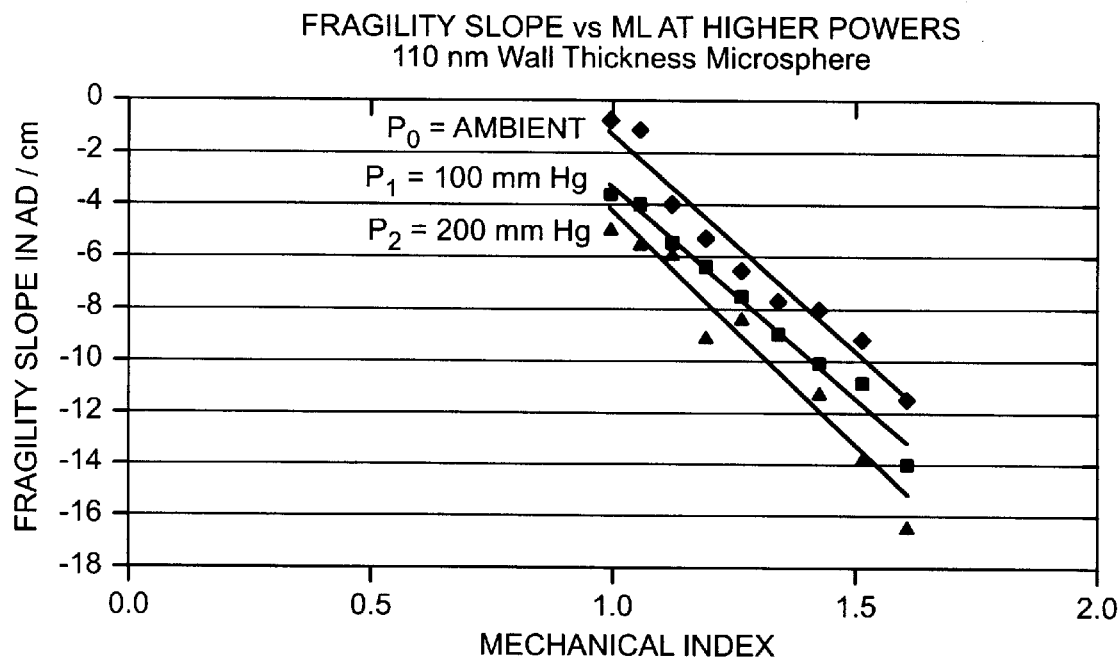
FIG._7
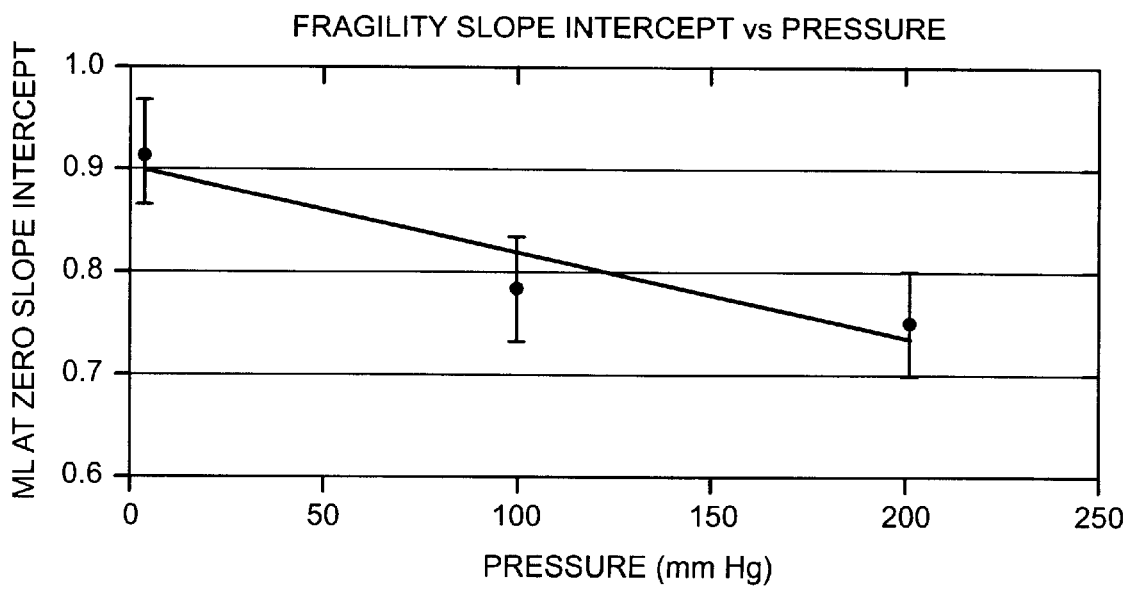
FIG._8

METHOD TO MEASURE AMBIENT FLUID PRESSURE

The present invention relates to a method for measuring real time ambient fluid pressure within a fluid-filled body cavity using gas-filled microbubbles and ultrasonic acoustic energy.

BACKGROUND OF INVENTION

Typically, cardiovascular pressures are measured using catheters which are introduced into the vascular systems via an artery or vein. Catheters exhibit a finite risk of both morbidity and mortality with routine usage in the clinical situation. More recently, sensor tipped guidewires to measure pressure have been developed. However, this procedure is also invasive with concomitant associations of morbidity and mortality. There are currently no adequately accurate direct, noninvasive real time clinical methods used to measure pressure in the cardiovascular system. An indirect method exists using Doppler ultrasound as suggested by Laaban, et al. (Laaban, J., Diebold, B., Zelinski, R., Lafay, M., Raffoul, H., and Rochemaure, J., *Chest* 96, (6): 1258–1262, 1989). With Doppler techniques, blood flow velocities are measured using ultrasonic scanners operating in the Doppler mode. By applying the Bernoulli equation and knowing the peak velocity, it is possible to calculate the pressure drop across a cardiac valve that created the flow. If one starts measurements in a vein such as the superior vena cava of known low pressure, one can calculate the pressure in the right ventricle and pulmonary artery and even make an estimate of the endiastolic left ventricular pressure with the technique. The indirect approach is filled with errors in difficult cases when good data is most needed and is used only for diagnosing the right side of the heart. Other non-invasive measurement schemes have been proposed (Blazek; Vladimir, Schmitt; Hans-J., U.S. Pat. No. 5,447,161; Aakhus, S., Soerlie, C., Faanes, A., Hauger, S. O., Bjoemstad, K., Hatle, L., and Angelsen, B. A. J., *American Journal of Cardiology*, 72: 260–267, 1993; Kyriakides, Z. S., Kremastinos, D. T., Rentoukas, E., Vavelidis, J., Damianou, C., and Toutouzas, P., *International Journal of Cardiology*, 33: 267–274, 1991; Neuman, A., Soble, J. S., Anagnos, P. C., Kagzi, M., and Parrillo, J. E., *Journal of the American Society of Echocardiography*, 11(2): 126–131, 1998) but show no significant advancement to the field.

In U.S. Pat. No. 3,640,271 to Horton, there is presented the concept of injecting a single bubble of known size into a patient for the purpose of measuring blood pressure. The concept was to stimulate the bubble into resonance ultrasonically and from the received backscattered signal, determine the resonant frequency of the bubble. It is further known that if both the diameter of the bubble and the resonant frequency are known, then the unknown pressure could be calculated. However, it is not known that the precision sized bubbles required for the technical approach have ever been achieved. Also, at present, it would be nearly impossible to locate bubbles within a specific organ or cavity for the very low concentration of bubbles required by the technology.

In Pat. No. 4,265,251 to Tickner, the concept of encapsulating a pressurized bubble within a fused saccharide shell is presented. The shell begins to dissolve in the circulatory system, thinning the wall. At some point in its dissolution, the shell fractures and the bubble escapes and expands. In so doing, it over-expands from its encapsulated diameter which sets it to free-ringing. A passive external transducer detects the free ringing signals and, by applying the same equations identified by Horton, computes the pressure. A limitation to the technology for usable clinical practice is the inability to control the point of rupture and the lack of precision (Osterle S., Sahines, T., Tucker, C., Tickner, E., et al., *The Western Journal of Medicine*, 1985 Ott; 143: 463–468.

In U.S. Pat. No. 5,749,364 to Sliwa, the concept for mapping cardiac pressures is presented by injecting a population of non-precision microspheres into the blood pool. Theory indicates that the resonant frequency peak of an encapsulated bubble is mathematically related to the ambient pressure. By examining the backscattered signal of the microspheres and from the change in their frequency spectrum, a map of the pressure in at least two dimensions is derived. One claimed method for doing this is to inject two microsphere population types, which exhibit different backscatter characteristics, and then use these different characteristics to deduce ambient pressures. Other work in using frequency shift has been explored. However, no clinical applications are known to have been developed (Ishihara, K., Kitabatake, A., Tanouchi, J., Fujii, K., Uematsu, M., Yoshida, Y., Kamada, T., Tamura, T., Chihara, K., and Shirae, K., *Jpn. J. Appl. Phys.*, 27(Suppl 27-1): 125–127, 1988) possibly due to the difficulties in measuring in-vivo frequency shifts. Furthermore, commercial ultrasound scanners have relatively narrow frequency bandwidths, which would not allow for the frequency range scan needed to detect changes in resonant frequency, especially in a formulation with multiple microsphere populations with attendant multiple resonance peaks.

In PCT No. 98/32378 (De Jong, N., Frinking, P., PCT No. WO 98/32378, Jul. 30, 1998; Bouakaz, A., Frinking, P., De Jong, N., Non-Invasive Pressure Measurement in a Fluid Filled Cavity, Abstract: The Fourth Heart Centre Symposium on Ultrasound Contrast Imaging, Jan. 21–22, 1999) there is disclosed the use of the decay of free gas bubbles to measure ambient pressure or temperature. The decay time of the gas bubble is dependent on the gas type, the liquid characteristics, the solubility of the gas within the liquid, the excitation frequency and the ambient temperature and pressure. However, in their scheme the microsphere is used only as a transport mechanism which releases the free bubble upon insonation and the properties of the free bubble are utilized for pressure measurement. They propose using a series of intermittent high power pulses to break the capsule of the microsphere, releasing the gas bubble and then using a series of intermittent low power pulses to determine the decay time of the bubble and therefore calculate pressure or temperature. Although the mechanism described uses a power level to rupture the capsule that is above a threshold, the fragility or release mechanism of the microsphere capsule itself is not controlled. Furthermore, if the microsphere has a very weak capsule, breakage of the capsule can occur at very low ultrasound powers. This leads to a response which is not controlled relative to imaging depth and applied power.

SUMMARY OF THE INVENTION

The present invention is directed to a method for measuring real time pressure in a region of interest in a fluid-filled body cavity. A composition of gas-containing microbubbles is introduced into the cavity, the microbubbles having a predetermined fragility threshold where the fragility threshold is correlated with the rupture response to fluid pressure, applied acoustic pressure, or a combination of both fluid and applied acoustic pressures. The acoustic pressure is applied from an ultrasonic energy producing source. The composition of microbubbles has predetermined acoustic response properties correlating to ambient pressure of the surrounding fluid. When the microbubbles are at the region of interest, an ultrasonic signal is applied at a power level sufficient to cause acoustic pressure sufficient to destroy or disrupt the membrane of the encapsulated microbubble population having a fragility threshold below the applied power level. Then, the ultrasound backscatter response is detected from the population of intact and failing microbubbles remaining at the region of interest and the backscatter signals are correlated to the predetermined acoustic response properties of the microbubble composition to determine the ambient pressure at the region of interest.

BRIEF DESCRIPTION OF THE DRAWINGS

FIG. 1 is a plot of average acoustic density versus ambient fluid pressure of microbubbles tested in Example 1;

FIG. 2 is a plot of power Doppler plume length versus ambient fluid pressure of the test on microbubbles tested in Example 2;

FIG. 3 is a plot of mean acoustic density versus distance, defining the fragility slope of the microbubbles tested in Example 4;

FIG. 4 is a plot of the fragility slopes of three microbubble compositions versus mechanical index as described in Example 4 to define the fragility curve;

FIG. 5 is a graph showing the fragility thresholds of three different microbubble compositions having three different wall thickness;

FIG. 6 is a plot of the backscatter signal versus mechanical index at three different pressures of a microbubble composition having 110 nm wall thickness;

FIG. 7 is a plot of fragility slopes versus mechanical index of a microbubble composition having 110 nm wall thickness at three different pressures;

FIG. 8 is a plot of the fragility slope intercept versus pressure from the data shown in FIG. 7.

DESCRIPTION OF THE PREFERRED EMBODIMENTS

As used herein the term microbubbles is intended to include microspheres, microcapsules and microparticles which are hollow and enclosing a core which may be filled with a gas. This may be a matrix material. It is not necessary for the microbubbles to be precisely spherical although they generally will be spherical and described as having average diameters. If the microbubbles are not spherical, then the diameters are referred to or linked to the diameter of a corresponding spherical microparticle having the same mass and enclosing approximately the same volume of interior space as a non-spherical microbubble. Microbubbles may be comprised of surface tension stabilized gas bubbles, surfactant stabilized gas bubbles, lipids and lipisomes, synthetic polymers and biopolymers; and may further comprise one or more layers of suitable material.

Ultrasonic backscatter of gas filled microbubbles and bubble resonance are well known in the ultrasound contrast field. It is known from the bubble resonance equations that resonant frequency and pressure are mathematically related. Theory indicates that an encapsulated gas bubble under insonation has a spectral envelope with a pronounced peak value at microbubble resonance and this aspect leads to the prior art methods of using resonant frequency shifts to determine pressure. However, in simulations with commercially available microbubble contrast agents, a nearly flat frequency response has been measured and reported by Boualaz, et al., (Bouakaz, A., DeJong, N., Cachard, C., and Jouini, K., *Ultrasonics* 36: 703–708, 1998). Thus, using frequency shift, it may be difficult to estimate in-vivo pressure.

To overcome the microbubble resonance detection problem, this invention focuses on the encapsulated bubble property of capsule fragility. The capsule of a microbubble can structurally fail from both static and dynamic pressure or combinations of the two. The ultrasonic waves can then disrupt or disintegrate the freed/escaping gas bubbles sufficiently to decrease their backscattering cross-section.

The intensity of backscattered signals depends upon the number of bubbles present in the sample volume and the size of the bubbles. If the size of the microbubble population is constant, then if capsules are broken for any reason and the encapsulated gas within dissolves or disintegrates into smaller bubbles, there is a concomitant decrease in backscattered signal intensity.

In the case of a gas filled microbubble used in the method of the present invention, the materials of the capsule wall, and the properties of those materials are selected and prepared to allow for the rupture of the capsule at critical or threshold pressures or within defined pressure limits. The microbubbles prepared in this manner are referred to herein as having engineered fragility. By fabricating a microbubble agent with a specifically designed fragility response and by controlling the applied ultrasound power, one can selectively rupture a gas containing microbubble, releasing the gas bubble, which then dissolves or breaks up under insonation in the ambient fluid. Since backscatter depends upon the presence of gas bubbles or gas containing microbubbles and their ability to re-radiate incident signals, backscatter signal intensity is decreased when the population of microbubbles or free bubbles decreases or the diameter of the bubbles decreases. However, in order to alter the backscatter on a clinically useable timescale, it becomes necessary to both structurally fail the capsule wall and have the released gas bubble dissolve or disintegrate quickly in the blood stream. The method herein disclosed takes advantage of this process by using the decrease in signal intensity and/or amplitude as a means of identifying the unknown pressure, instead of the shift in resonant frequency or decay time of a free gas bubble. Since microbubbles can be seen within cardiac chambers and even destroyed by ultrasonic imaging scanners, the present invention provides a viable way for measuring pressure in real time provided that the microbubbles are designed and fabricated to meet certain specifications. These specifications concern the relationship between static and dynamic stresses within the membrane or capsule shell that when exceeded cause structural failure. The released free gas bubble should quickly dissolve or disintegrate into much smaller bubbles so as not to continue to backscatter incident signals.

Accordingly, having prepared microbubble compositions with engineered fragility, such compositions are used to measure the real time ambient fluid pressure at a region of interest in a fluid-filled cavity, such as the heart. Typically the microbubble composition will be introduced into the blood system and the location of the composition within the body can be monitored by conventional ultrasound scanning. At the region of interest, acoustic pressure can be applied by a focused ultrasound source to rupture the capsules of the microbubbles which have a fragility threshold below the power level of the applied acoustic pressure. Then the ultrasound backscatter response from the remaining population of intact microbubbles or disintegrating gas bubbles at the region of interest is made and correlated to predetermined acoustic response properties of the microbubble composition to determine the ambient pressure at the region of interest. The results may be displayed as a qualitative or quantitative pressure map using greyscale or color overlays of the base image.

In general, the ambient pressure at a region of interest can be determined by correlating pressure to the acoustic energy required to rupture the capsule of the microbubbles. First, a predetermined correlation of acoustic energy, typically given as a mechanical index, to pressure is made. This may be experimentally determined by measuring the microbubble response under pressure at an acoustically targeted site. Fragility slopes of various populations may then be experimentally determined from the results of acoustic density vs. distance along a channel containing an acoustically interrogated population of flowing microbubbles. The fragility slopes are then plotted to derive fragility curves of fragility slope vs. mechanical index. There are substantially linear portions of each fragility curve which, when extended to the intercept at the zero fragility slope value, determine the mechanical index at the threshold fragility. This mechanical index correlates to the threshold fragility when the microbubbles rupture, and is dependent upon the ambient fluid pressure.

This can be accomplished by several methods. Since the microbubble formulations can be made with uniform properties, a fragility versus pressure characteristic of the composition may be predetermined by in vitro experiments to develop a response curve. In one such method when the composition is injected into the bloodstream, a focused ultrasound scanner is applied at a low power sound pulse or pulse train to establish a baseline. Then a second pulse or pulse train is applied at a higher power which is selected to destroy the segment of the microbubble population whose fragility threshold is below the power level of the second pulse. A third pulse or pulse train also at high power is then used to measure the post destruction backscatter response. The difference of the backscatter signal from the third pulse versus the baseline is a measure of the pressure in the ambient fluid and can be determined by reference to the response curve. The results may be displayed on the monitor of the ultrasound scanner as a real time overlay, either in greyscale or color.

Another method of utilizing the microbubbles to measure ambient pressure is to combine a microbubble composition fabricated from two or more populations of gas-filled microbubbles where each population comprises differing fragility thresholds. The fragility versus pressure characteristics of each population as well as the combined population are predetermined by in vitro experiments and the response curve is developed. After administering the formulation into the bloodstream by bolus injection or infusion, an ultrasound scanner is focused on the region of interest to apply successively increasing power pulses or pulse trains. At each power setting, that population of microbubbles whose fragility threshold is below the power level of the pulse will be destroyed. The decay in the intensity of the backscatter signal from each successive pulse is a measure of the pressure in the ambient fluid. The pressure measurement is calculated from this decay, referenced to the known response curve, and is displayed on the monitor.

Yet another method is to inject a single population of microbubbles having a population with a fragility threshold that is linearly decreasing with increasing ambient pressure and under constant applied ultrasound pressure. The fragility curve is determined by empirical analysis. An ultrasound scan of the cardiac chambers, for example, may be performed under a power Doppler mode at a constant power level so that the quantity of microbubble destruction within the chambers will be dependent upon the ambient pressure. Each destruction event of a microbubble will result in a decorrelation signal being detected and displayed by the ultrasound scanner. The intensity of the Power Doppler ultrasound display will be directly proportional to the ambient fluid pressure, by way of the predetermined response.

By yet another method, the pressure in the chamber of the heart or across a heart valve may be measured. The acoustic density value of a series of adjacent regions of interest are measured along a scanline axis of the ultrasound transducer a rapid sequence. The slope of a plot of the acoustical density versus distance along the scanline axis is determined and compared to predetermined values of the acoustical density versus pressure. The data can then be displayed as a pressure value along the scanline. By repeating the determination as subsequent scanlines, the pressure value for a region within the chamber can be determined and displayed.

An alternate method to measure pressure is as follows. A region of interest containing microbubbles of engineered fragility is interrogated with a series of ultrasound pulses in rapid succession of steadily increasing power values: $P_1$, $P_2, \ldots P_n$, and respective acoustic density or backscatter signal levels are determined: $B_1, B_2, \ldots B_n$. A fragility curve, as shown in Example 4 below, made by plotting the slope (taken from the results of acoustical density versus distance) versus mechanical index, is computed to determine the pressure from either the slope of the fragility curve which occurs in a nearly linear high power region or from a computed zero slope intercept as shown in Example 4 below. Comparing the data to a predetermined table of correlation to pressure will show pressure at the point of measurement. Real time display of the pressure can then be accomplished by the ultrasound scanner.

The microbubbles according to the present invention may be a surface tension or surfactant stabilized gas bubble or have a mono-layer shell but preferably have at least a bi-layered shell. The outer layer of the shell will be a biologically compatible material or biomaterial since it defines the surface which will be exposed to the blood and tissues within the body. The inner layer of the shell will be a biodegradable polymer, which may be a synthetic polymer, which may be tailored to provide the desired mechanical and acoustic properties to the shell. The cores of the microbubbles contain gas, typically air, nitrogen or a fluorocarbon gas. To make the microbubbles rupturable by ultrasound energy, they must contain a gas to allow acoustic coupling and particle oscillation. Microbubbles are constructed such that the majority of those prepared in a composition will have diameters within the range of about one to ten microns in order to pass through the capillary system of the body.

Since the microbubbles preferably have an outer and inner layer, the layers can be tailored to serve different functions. The outer shell which is exposed to the blood and tissues serves as the biological interface between the microbubbles and the body. Thus it will be made of a biocompatible material which is typically amphiphilic, that is, has both hydrophobic and hydrophilic characteristics. Blood compatible materials are particularly preferred. Such preferred materials are biological materials including proteins such as collagen, gelatin or serum albumins or globulins, either derived from humans or having a structure similar to the human protein, glycosoaminoglycans such as hyaluronic acid, heparin and chondroitin sulphate and combinations or derivatives thereof. Synthetic biodegradable polymers, such as polyethylene glycol, polyethylene oxide, polypropylene glycol and combinations or derivatives may also be used. The outer layer typically has a chemistry which allows charge and chemical modification. The versatility of the surface allows for such modifications as altering the charge of the outer shell, such as by selecting a type A gelatin having an isoelectric point above physiological pH, or by using a type B gelatin having an isoelectric point below physiological pH. The outer surfaces may also be chemically modified to enhance biocompatibility, such as by PEGylation, succinylation or amidation, as well chemically binding to the surface a targeting moiety for binding to selected tissues. The targeting moieties may be antibodies, cell receptors, lectins, selecting, integrins or chemical structures or analogues of the receptor targets of such materials. The mechanical properties of the outer layer may also be modified, such as by cross linking, to make the microbubbles suitable for passage to the left ventricle.

The inner shell will be a biodegradable polymer, which may be a synthetic polymer. An advantage of the inner shell is that it provides additional mechanical properties to the microbubble which are not provided or insufficiently provided by the outer layer or, enhances mechanical properties not sufficiently provided by the outer layer, without being constrained by surface property requirements. For example, a biocompatible outer layer of a cross-linked proteinaceous hydrogel can be physically supported using a high moduli synthetic polymer as the inner layer. The polymer may be selected for its modulus of elasticity and elongation, which define the desired mechanical properties. Typical biodegradable polymers include polycaprolactone, polylactic acid, polylactic-polyglycolic acid co-polymers, co-polymers of lactides and lactones, such as epsilon-caprolactone, delta-valerolactone, polyalkylcyanoacrylates, polyamides, polyhydroxybutryrates, polydioxanones, poly-beta-aminoketones, polyanhydrides, poly-(ortho)esters, polyamino acids, such as polyglutamic and polyaspartic acids or esters of polyglutamic and polyaspartic acids. References on many biodegradable polymers are cited in Langer, et. al. (1983) *Macromol.Chem.Phys.*C23, 61–125.

The inner layer permits the modification of the mechanical properties of the shell of the microbubble which are not provided by the outer layer alone. For use as an ultrasonic contrast agent, the inner layer will typically have thickness which is no larger than is necessary to meet the minimum mechanical requirements, in order to maximize the interior gas volume of the microbubble. The greater the gas volume within the microbubble the better the echogenic properties.

The combined thickness of the outer and inner layers of the microbubble shell will depend in part on the mechanical properties required of the microbubble, but typically the total shell thickness will be in the range of 25 to 750 nm.

The microbubbles may be prepared by an emulsification process to control the sequential interfacial deposition of shell materials. Due to the amphiphilicity of the material forming the outer layer, stable oil/water emulsions may be prepared having an inner phase to outer phase ratio approaching 3:1, without phase inversion, which can be dispersable in water to form stable organic phase droplets without the need for surfactants, viscosity enhancers or high shear rates.

Two solutions are prepared, the first being an aqueous solution of the outer biomaterial. The second is a solution of the polymer which is used to form the inner layer, in a relatively volatile water-immiscible liquid which is a solvent for the polymer, and a relatively non-volatile water-immiscible liquid which is a non-solvent for the polymer. The relatively volatile water-immiscible solvent is typically a C5–C7 ester, such as isopropyl acetate. The relatively non-volatile water-immiscible non-solvent is typically a C6–C20 hydrocarbon such as decane, undecane, cyclohexane, cyclooctane and the like. In the second solution containing the polymer for the inner layer, the polymer in water-immiscible solvents are combined so that the polymer fully dissolves and the two solvents are miscible with agitation. The polymer solution (organic phase) is slowly added to the biomaterial solution (aqueous phase) to form a liquid foam. Typically about three parts of the organic polymer solution having a concentration of about 0.5 to 10 percent of the polymer is added to one part of the aqueous biomaterial solution having a concentration of about 1 to 20 percent of the biomaterial. The relative concentrations of the solutions and the ratio of organic phase to aqueous phase utilized in this step essentially determine the size of the final microbubble and wall thickness. After thorough mixing of the liquid foam, it is dispersed into water and typically warmed to about 30–35° C. with mild agitation. While not intending to be bound by a particular theory, it is believed that the biomaterial in the foam disperses into the warm water to stabilize an emulsion of the polymer in the organic phase encapsulated within a biomaterial envelope. To render the biomaterial envelope water insoluble, a cross linking agent, such as glutaraldehyde, is added to the mixture to react with the biomaterial envelope and render it water insoluble, stabilizing the outer shell. Other cross-linking agents may be used, including the use of carbodiimide cross-linkers.

Since at this point the inner core contains a solution of a polymer, a solvent and a non-solvent with different volatilities, as the more volatile solvent evaporates, or is diluted, the polymer precipitates in the presence of the less volatile non-solvent. This process forms a film of precipitate at the interface with the inner surface of the biomaterial shell, thus forming the inner shell of the microbubble after the more volatile solvent has been reduced in concentration either by dilution, evaporation or the like. The core of the microbubble then contains predominately the organic non-solvent. The microbubbles may then be isolated by centrifugation, washed, formulated in a buffer system, if desired, and dried. Typically, drying by lyophilization removes not only the non-solvent liquid core but also the residual water to yield gas-filled hollow microbubbles.

It may be desirable to further modify the surface of the microbubble, for example, in order to passivate surfaces against macrophages or the reticuloendothelial system (RES) in the liver. This may be accomplished, for example by chemically modifying the surface of the microbubble to be negatively charged since negatively charged particles appear to better evade recognition by macrophages and the RES than positively charged particles. Also, the hydrophilicity of the surface may be changed by attaching hydrophilic conjugates, such as polyethylene glycol (PEGylation) or succinic acid (succinylation) to the surface, either alone or in conjunction with the charge modification.

The biomaterial surface may also be modified to provide targeting characteristics for the microbubble. The surface may be tagged by known methods with antibodies or biological receptors.

The microbubbles may also be sized or processed after manufacture. This is an advantage over lipid-like microbubbles which may not be subjected to mechanical processing after they are formed due to their fragility.

The final formulation of the microbubbles after preparation, but prior to use, is in the form of a lyophilized cake. The later reconstitution of the microbubbles may be facilitated by lyophilization with bulking agents which provide a cake having a high porosity and surface area. The bulking agents may also increase the drying rate during lyophilization by providing channels for the water and solvent vapor to be removed. This also provides a higher surface area which would assist in the later reconstitution. Typical bulking agents are sugars such as dextrose, mannitol, sorbitol and sucrose, and polymers such as PEG's and PVP's.

It is undesirable for the microbubbles to aggregate, either during formulation or during later reconstitution of the lyophilized material. Aggregation may be minimized by maintaining a pH of at least one to two pH units above or below the isoelectric point($P_i$) of the biomaterial forming the outer surface. The charge on the surface is determined by the pH of the formulation medium. Thus, for example, if the surface of the biomaterial has a $P_i$ of 7 and the pH of the formulation medium is below 7, the microbubble will possess a net positive surface charge. Alternatively, if the pH of the formulation medium is greater than 7, the microbubble would possess a negative charge. The maximum potential for aggregation exist when the pH of the formulation medium approaches the $P_i$ of the biomaterial used in the outer shell. Therefore by maintaining a pH of the formulation medium at least one to two units above or below the $P_i$ of the surface, microbubble aggregation will be minimized. As an alternative, the microbubbles may be formulated at or near the $P_i$ with the use of surfactants to stabilize against aggregation. In any event, buffer systems of the final formulation to be injected into the subject should be physiologically compatible.

The bulking agents utilized during lyophilization of the microbubbles may also be used to control the osmolality of the final formulation for injection. An osmolality other than physiological osmolality may be desirable during the lyophilization to minimize aggregation. However, when formulating the microbubbles for use, the volume of liquid used to reconstitute the microbubbles must take this into account.

Other additives may be included in order to prevent aggregation or to facilitate dispersion of the microbubbles upon formulation. Surfactants may be used in the formulation such as poloxomers (polyethylene glycol-polypropylene glycol-polyethylene glycol block co-polymers). Water soluble polymers also may assist in the dispersion of the microbubbles, such as medium molecular weight polyethyleneglycols and low to medium molecular weight polyvinylpyrolidones.

It will be realized that various modifications of the above-described processes may be provided without departing from the spirit and scope of the invention. For example, the wall thickness of both the outer and inner layers may be adjusted by varying the concentration of the components in the microbubble-forming solutions. The mechanical properties of the microbubbles may be controlled, not only by the total wall thickness and thicknesses of the respective layers, but also by selection of materials used in each of the layers by their modules of elasticity and elongation, molecular-weight, hoop strength, and degree of cross-linking of the layers. Hoop strength being defined as a mechanical property of a sphere based on the resistance of a section on the sphere to radial force. Mechanical properties of the layers may also be modified with plasticizers or other additives. Adjustment of the strength of the shell may be modified, for example, by the internal pressure within the microbubbles.

Precise acoustical characteristics of the microbubble may be achieved by control of the shell mechanical properties, thickness, as well as size distribution. The microbubbles may be ruptured by ultrasonic energy to release gases trapped within the capsule into the blood stream. In particular, by appropriately adjusting the mechanical properties, the particles may be made to remain stable to threshold diagnostic imaging power, while being rupturable by an increase in power and/or by being exposed to its resonant frequency. The resonant frequency may be made to be within the range of transmitted frequencies of diagnostic body imaging systems or may be a harmonic or subharmonic of such frequencies. During the formulation process the microbubbles may be prepared to contain various gases, including blood soluble or blood insoluble gases.

The preferred embodiment is a bi-layered microbubble with a biopolymer outer shell and a synthetic polymer inner layer.

Typical diagnostic or therapeutic targets for microbubbles of the invention are the heart, liver, kidney, vascular system and tumors.

The following examples are provided by way of illustration, and are not intended to limit the invention in any way.

EXAMPLE 1

A Hewlett Packard SONOS 2500 ultrasonic scanner was used. This scanner has the capability of measuring the acoustic density (AD)as a function of time within a region of interest (ROI) displayed on the video monitor. The scanner was set in the 2D harmonic mode with send frequency of 1.8 MHZ and receive frequency of 3.6 MHZ. A test cell was constructed comprising a 3.8 mm diameter cellulose tubing (the imaging tube)running through a plastic beaker approximately 3 cm below the top. Degassed water was used to fill the beaker. A flow system was connected to the imaging tube consisting of a mixing reservoir with microsphere contrast agent suspended in it, a peristaltic pump and a pressure transducer with digital readout. A backpressure valve was placed on the drain end of the tube to be able vary the system pressure. The transducer focus was set on the center of the imaging tube and the ROI placed within the image of the tubing lumen. The scanner was set in the AD mode and the AD readings were recorded by the scanner. The system was run with zero back pressure to establish a baseline and then the discharge flow valve was closed to achieve a desired pressure and the procedure repeated. Pressures were increased to roughly 200 mm Hg and then decreased during the study.

Several different gas containing microbubble agents were employed and all yield a linear relationship as exemplified in FIG. 1. Also, several different power values (mechanical index or "MI")were utilized. In all cases, a linear decrease of AD was observed as a function of pressure for a fixed MI, thus demonstrating selective fragility.

EXAMPLE 2

Hewlett Packard SONOS 5500 ultrasound scanner was used in conjunction with a an ATS Laboratories, Model 524 Doppler Flow Phantom. The setup was essentially the same as Example 1. However, the scanner was set up in the Angio (Power Doppler or Doppler decorrelation) mode. In this mode, decorrelation events as determined by Doppler signal processing above a preset threshold are displayed on the monitor of the ultrasound scanner. The flow phantom consists of a housing filled with an elastomer which is designed to mimic the attenuation of living tissue and has four flow channels of 2, 4, 6, & 8 mm diameter respectively running through it. The 6 mm diameter channel of the flow phantom was chosen. The sector scan transducer was oriented along the centerline of the flow tube. When operated in the Angio mode and when microbubbles are present in the flow tube of the phantom, a colored plume derived from the decorrelation events is displayed on the monitor. The plume corresponds to the disruption or disintegration of microbubbles within the scanned ultrasound field. All tests were performed with a pulse repetition frequency of 1.2 kHz, an triggering interval of 2000 ms, 8 pulse Doppler packet and various values of TIS (Thermal Index, Soft tissue: a measure of output power) and various formulations microbubbles having an outer layer of albumin and an inner layer of d, 1 lactide. Using the caliper function of the system, one can measure the distance from the first point of insonation to the end of the plume on the centerline of the channel. Very fragile microbubbles fail instantly as they enter the sound field and the plume is very short, typically only a few millimeters, whereas more durable microbubbles produce a plume which can extend across the image. Since the plume changes with number of decorrelation events, a measure of, agent fragility is accomplished and one can then examine the results under varying ambient pressures. By adjusting the discharge (backpressure) valve, one can take measurements of the plume length with varying pressure. If the microbubbles exhibit engineered fragility properties, the plume length should change under differing pressure conditions which are dependent upon the properties of the microbubbles. Indeed this is the case as exemplified in the FIG. 2.

As can be seen in FIG. 2, there is a linear decrease in plume length with pressure with a correlation coefficient of 0.98. This particular test did not require high power levels. The tests were performed under various power conditions ranging from a TIS value of 0.2 to 1.0 and in all cases tested there was a linear relationship between plume length and pressure.

EXAMPLE 3

The set-up as presented in Example 2 above was used with the exception that the flow phantom was exchanged for a 6.5 cm diameter by 7.6 cm high acrylic cylindrical phantom chamber with a sealed top and bottom. A magnetic stirring bar was placed in the chamber and the chamber filled completely with de-gassed water. Two ports with luer lock syringe fittings are present to allow connection to the chamber. One port is connected to the pressure transducer, and the other port connected through a 3-way valve to a pressurizing syringe and a sample injection syringe. The S4 transducer of the HP 5500 scanner was placed in a water-filled well on the top of the chamber, imaging directly downward through a thin acrylic cover. The HP SONOS 5500 was run in Angio mode and in B-mode Harmonic. The transducer focus was set at 4 cm in depth, near the mid chamber position. A diluted sample of gas filled, dual walled microbubbles (described in Example 8) was injected into the chamber with the pressure transducer port open to relieve the pressure build-up from sample introduction. The pressure transducer port was closed and the 3-way valve switched to the pressurizing syringe, which is filled with water. The chamber is placed on a magnetic stirrer set to slow speed.

The ultrasound scanner was turned on and the Power Doppler image displayed is of a somewhat spherical region of signals from Doppler decorrelation events within the central region of the phantom. The pressurizing syringe is then engaged to bring the pressure up to approximately 150 to 200 mm Hg and back to ambient at approximately 30 cycles per minute. The display shows the region of decorrelation signals diminishing in size significantly with the increase in pressure and returning to baseline as the pressure returns to ambient. The image changes indicate the correspondence of the Doppler decorrelation signals to the ambient pressure. The results were recorded to videotape.

EXAMPLE 4

Using the set-up with the HP SONOS 5500 and Doppler Flow Phantom as detailed in Example 2 above, a test was performed to determine the variations in fragility thresholds and their relationship to ambient pressure of microbubbles fabricated with differing wall thickness. Three samples of microbubbles (described in Example 8) were fabricated with polylactide inner walls of thickness approximately 28, 55 and 110 nm respectively. The samples were interrogated using B-mode Harmonic imaging at 1.8 MHz send and 3.6 MHz receive frequencies. Using the AD function, an ROI was placed at the input end of the image of the flow channel and densitometry readings taken at each increment. The ROI was moved laterally, in increments along the flow direction and readings taken. The resultant graph, FIG. 3, shows the exemplary results for one sample (55 nm thickness) as a function of mean AD value versus distance in centimeters along the flow channel. The slope of this line is called the Fragility Slope (FS). The results from all samples indicate a linear decrease in backscattered signal with distance from the source, and exposure to the ultrasound field.

The test is repeated at MI values from 0.0 to 1.6, in increments of 0.1 MI. The slopes of the resultant measurements are then plotted versus the power or MI value, as shown in FIG. 4. This curve is termed the Fragility Curve (FC). All three samples show a region at low power levels where the slopes are essentially zero, then a power level where the decrease in signal from the destruction of microcapsules begins. Determining the curve intercepts with the zero slope value as shown in FIG. 5, yields fragility threshold values for the various samples.

Values of AD vs Distance (FIG. 3) were determined at ambient and at approximately 100 and 200 mm Hg respectively. The y-intercept of FIG. 3 was taken as an indication of peak backscatter signal. The peak AD backscatter signal was then plotted versus MI at the three test pressures in FIG. 6. The curves are roughly equal indicating that the agent is stable under the test pressures examined and exhibits the same acoustic behavior at each pressure, and furthermore that agent concentrations in each test were comparable.

Fragility Slopes and resultant Fragility Curves for the 110 nm wall thickness sample where generated at different pressures as above. Taking the data in the high MI region, from 1.0 to 1.6, wherein the behavior of the Fragility Curve is nearly linear, three distinct linear results are seen as in FIG. 7. The intercept of these lines with the zero slope value is shown in FIG. 8. These curves may be used to compute the ambient pressure of the fluid.

EXAMPLE 5

Preparation of Gelatin Polycaprolactone Microbubbles

A solution of 1.0 gms gelatin (275 bl, isoelectric point of 4.89) dissolved in 20 ml deionized water was prepared at approximately 60 C. Native pH of the solution was 5.07.

Separately, 1.0 gms polycaprolactone (M.W. 50,000) and 6.75 ml cyclooctane was dissolved in 42 ml isopropyl acetate with stirring at approximately 70 C. After cooling to 37 C., the organic mixture was then slowly incorporated into the gelatin solution maintained at 30 C. and under moderate shear mixing using a rotary mixer. Once the organic phase was fully incorporated, the mixing rate was increased to 2,500 rpm for 5 minutes and then stirred at low shear for an additional 5 minutes. The resulting o-w emulsion was then added with stirring to 350 ml deionized water maintained at 30 C. and containing 1.2 ml 25% gluteraldehyde. Immediately after the addition of the emulsion, the bath pH was adjusted to 4.7. After 30 minutes, the pH was adjusted to 8.3. Low shear mixing was continued for approximately 2½ hours until the isopropyl acetate had completely volatilized. Polyoxamer 188 in the amount of 0.75 gm was then dissolved into the bath. The resulting microbubbles were retrieved by centrifugation and washed 2 times in an aqueous solution of 0.25% polyoxamer 188.

Microscopic inspection of the microbubbles revealed spherical capsules having a thin-walled polymer shell encapsulating a liquid organic core. Staining the slide preparation with coomassie blue G indicated the presence of an outer protein layer uniformly surrounding the polymer shell.

The particle size spectrum was determined using a Malvern Micro. Median diameter was 4.78 microns with a spectrum span of 0.94.

EXAMPLE 6

Preparation of Microbubble Agent Formulation

A quantity of microbubbles prepared in a manner similar to example 5 were suspended into an aqueous solution of 25 mM glycine, 0.5% pluronic f-127, 1.0% sucrose, 3.0% mannitol, and 5.0% PEG-3400. The suspension was then lyophilized. The resulting dry powder was reconstituted in deionized water and examined under the microscope to reveal that the microbubbles now contained a gaseous core. Staining the preparation with commassie blue G confirmed that the outer protein layer surrounding the capsules was intact and had survived the lyophilization process.

Echogenicity was confirmed by insonating at both 2½ and 5 MHZ a quantity of lyophilized microbubbles dispersed in 120 ml deionized water. Measurement was taken at least 15 minutes after dispersion of the microbubbles to insure that the back scattered signal was due solely from the gas contained within the microbubbles. The B mode display showed a high contrast indicating that the microbubbles were gas filled.

EXAMPLE 7

Preparation of Albumin Polycaprolactone Microbubbles

A 6% aqueous solution was prepared from a 25% solution of USP grade human serum albumin (Alpha Therapeutic Corp) by dilution with deionized water. The solution was adjusted to a pH of 3.49 using 1 N HCl. Separately, 8 parts by weight polycaprolactone (M.W. 50,000) and 45 parts cyclooctane were dissolved in 300 parts isopropyl acetate at approximately 70° C. Once dissolution was complete, the organic solution was allowed to cool to 37° C. With mild stirring, 42.5 gm of the prepared organic solution was slowly incorporated into 25.0 gm of the albumin solution while the mixture was maintained at 30° C. The resulting coarse o-w emulsion was then circulated through a stainless steel sintered metal filter element having a nominal pore size of 7 microns. Recirculation of the emulsion was continued for 8 minutes. The emulsion was then added with stirring to 350 ml deionized water maintained at 30° C. and containing 1.0 ml of 25% gluteraldehyde. During the addition, the pH of the bath was monitored to insure that it remained between 7 and 8. Final pH was 7.1. Low shear mixing was continued for approximately 2½ hours until the isopropyl acetate had completely volatilized. Poloxamer 188 in the amount of 0.75 gm was then dissolved into the bath. The resulting microbubbles were retrieved by centrifugation and washed 2 times in an aqueous solution of 0.25% poloxamer.

Microscopic inspection of the suspension revealed spherical particles having a thin-walled polymer shell with an outer protein layer and an organic liquid core. The peak diameter as, determined by the Malvern Micro particle size analyzer, was 4.12 microns.

The suspension was then lyophilized in a manner similar to that described in Example 6. The resulting dry cake was reconstituted with deionized water and examined under the microscope to reveal that the microbubbles were spherical, discrete, and contained a gaseous core.

EXAMPLE 8

Preparation of Albumin Polylactide Microbubbles

A 6% aqueous solution was prepared from a 25% solution of USP grade human albumin by dilution with deionized water. Ion exchange resin ( AG 501-X8, BioRad Laboratories) was then added to the solution at a ratio of 1.5 gm resin to 1.0 gm dry weight of albumin. After 3 hours the resin was removed by filtration and the pH of the solution was adjusted from 4.65 to 5.5. Separately, 0.41 gm d-1 lactide (0.69 dL/gm in CHCl$_3$: at 30° C.) and 5.63 gm cyclooctane were dissolved in 37.5 gm isopropyl acetate. The organic solution was then slowly incorporated into 25.0 gm of the prepared albumin solution with mild stirring while the mixture was maintained at 30° C. The resulting coarse o-w emulsion was then circulated through a stainless steel sintered metal filter element having a nominal pore size of 7 microns. Recirculation of the emulsion was continued for 8 minutes. The emulsion was then added with stirring to 350 ml deionized water maintained at 30 C. and containing 1.0 ml of 25% gluteraldehyde. During the addition, the pH of the bath was monitored to insure that it remained between 7 and 8. Final pH was 7.0. Low shear mixing was continued for approximately 2½ hours until the isopropyl acetate had completely volatilized. Polyoxamer 188 in the amount of 0.75 gm was then dissolved into the bath. The resulting microbubbles were retrieved by centrifugation and washed 2 times in an aqueous solution of 0.25% polyoxamer.

Microscopic inspection revealed hollow spherical polymer microbubbles having an outer protein layer and an inner organic liquid core. The suspension was formulated with a glycine/PEG 3350 excipient solution, then lyophilized. The resulting dry cake was reconstituted with deionized water and examined under the microscope to reveal that the microbubbles were spherical, discrete, and contained a gaseous core.

EXAMPLE 9

PEG Modification of the Microbubble Surface

Microbubbles were prepared in a manner similar to Example 7. After centrifugation, 4 ml of the microbubbles containing cream (approximately 11 ml total yield) was resuspended in 31 ml deionized water. To this was added a 10 ml solution containing 0.3 gm methoxy-peg-NCO 5000 and the pH was adjusted to 8.7. The mixture was allowed to react at room temperature with mild agitation for 4½ hours. At the end of this period the pH was measured to be 7.9. The microbubbles were retrieved by centrifugation and washed 2 times in a 0.25% solution of polyoxamer 188. The suspension was formulated with a glycine/PEG 3350 excipient solution, then lyophilized. The resulting dry cake was reconstituted with deionized water and examined under the microscope to reveal that the microbubbles were spherical, discrete, and contained a gaseous core.

EXAMPLE 10

Preparation of Wall Modified Albumin Polycaprolactone Microbubbles

Albumin coated microbubbles were prepared in a manner similar to Example 7 with the exception that 0.20 gm paraffin was also dissolved into the organic solution along with the polycaprolactone and the cyclooctane.

Microscopic inspection of the finished microbubble suspension revealed spherical particles having a morphology and appearance virtually identical to those prepared without the addition of paraffin.

EXAMPLE 11

During a patient examination, the physician injects a bolus of microbubble pressure agent intravenously. Using the ultrasound scanner, the physician images the chambers of the heart, primarily the left ventricle. With the scanner focused within the left ventricle and electrocardiogram (ECG) leads attached to the patient, the physician sets the scanner in Power Doppler (Doppler Decorrelation) mode. The ultrasound scanner is set-up to trigger based on ECG input, with the trigger point near to or at the end of diastolic cycle. The intensity of the image is correlation to the ambient pressure by way of a predetermined response of the microbubble agent. The resultant image intensity, when compared to the predetermined response, yields the end diastolic left ventricular pressure. This information is especially useful in determine cardiac ejection fraction which is a measure of the output of the heart.

What is claimed is:

1. A method for measuring ambient pressure at a region of interest in a fluid-filled body cavity or vessel comprising the steps of:
   (a) introducing into said cavity or vessel a composition of gas-containing microbubbles, said microbubbles having a predetermined fragility threshold, said fragility threshold correlating the disintegration response of said microbubbles to a combination of fluid and applied acoustic pressure, said acoustic pressure being applied from an ultrasonic energy producing source and said composition having predetermined acoustic response properties correlating to ambient pressure of a surrounding fluid;
   (b) applying an ultrasonic signal at said region of interest within said cavity or vessel at a power level sufficient to cause acoustic pressure to disintegrate a microbubble population, said power level being above or equal to said predetermined fragility threshold;
   (c) detecting the returned acoustic signals backscattered from the population of disintegrating and intact microbubbles remaining at said region of interest;
   (d) correlating said returned acoustic signals to said predetermined acoustic response properties of said composition to determine said ambient pressure at said region of interest;
   (e) repeating steps (a)–(b).

2. A method according to claim 1 further comprising the step of displaying said correlation on a monitor of an ultrasound scanner.

3. A method according to claim 1 wherein said microbubbles are characterized by having a shell comprising one or more layers.

4. A method according to claim 3 wherein in step (a) the predetermined fragility of each of said microbubbles is controlled by selecting the thickness of one or more layers of the shell.

5. A method according to claim 3 wherein in step (a) the predetermined fragility threshold of said microbubbles is controlled through the use of materials in the shell of differing moduli of elasticity.

6. A method according to claim 3 wherein in step (a) the predetermined fragility threshold of said microbubbles is controlled through use of materials in the shell of differing molecular weight.

7. A method according to claim 3 wherein in step (a) the predetermined fragility threshold of said microbubbles is controlled through use of materials in the shell of differing hoop strength.

8. A method according to claim 3 wherein in step (a) the disintegration response of said microbubbles approximates a step function at one or more pressure levels.

9. A method according to claim 1 wherein said gas in said microbubbles comprises physiologically acceptable gas.

10. A method according to claim 9 wherein said gas comprises nitrogen.

11. A method according to claim 9 wherein said gas comprises air.

12. A method according to claim 9 wherein said gas comprises a fluorocarbon compound.

13. A method according to claim 1 wherein said composition is introduced into said cavity as a bolus.

14. A method according to claim 1 wherein said composition is introduced to said cavity as a controlled rate infusion.

15. A method according to claim 1 wherein in step (a) the disintegration response is a linear relationship with ambient pressure in combination with constant ultrasound pressure.

16. A method according to claim 1 wherein said step of applying an ultrasonic signal and said step of detection are accomplished with an ultrasound imaging system.

17. A method according to claim 16 wherein the returned acoustic signals of said microbubbles is detected utilizing B-mode harmonic imaging methods.

18. A method according to claim 16 wherein the returned acoustic signals of said microbubbles is detected utilizing power Doppler decorrelation imaging methods.

19. A method according to claim 18 wherein the ambient fluid pressure is determined by comparing the intensity of the returned power Doppler decorrelation signal and the predetermined acoustic response properties of said microbubbles.

20. A method according to claim 19 wherein the ambient fluid pressure result is displayed in real time.

21. A method according to claim 19 wherein the ambient fluid pressure result is displayed as a greyscale map of ambient pressure within said body cavity. map of ambient pressure.

22. A method according to claim 19 wherein the ambient fluid pressure result is displayed as a color map of ambient pressure within said body cavity.

23. A method according to claim 22 wherein the colors of the color map are coded to the amplitude of the ambient pressure.

24. A method according to claim 19 wherein the results are displayed as a map of ambient pressure and correlated to a predetermined electrocardiogram of the subject to display pressure as a function of time point within the cardiac cycle.

25. A method according to claim 1 wherein said composition comprises two or more population of microbubbles of differing fragility thresholds.

26. A method according to claim 1 wherein the response of said microbubbles is detected by way of interrogation with an ultrasound signal of a first low power signal to establish a baseline and a second higher power signal to disintegrate the microbubble population whose fragility threshold is below said second power level and with a subsequent third high power signal to measure the resultant signal.

27. A method according to claim 25 wherein the ultrasound signal comprises a single pulse train wherein the two differing power levels are produced such that a first low power pulse is sent at the beginning of said pulse train and second and third high power pulses at the middle and the end of said pulse train, respectively.

28. A method according to claim 25 wherein the ultrasound signal comprises two or more pulse trains wherein the first pulse train is of low power and subsequent pulse trains are of higher power.

29. A method according to claim 25 wherein the ultrasound signal comprises three or more pulse trains wherein the first pulse train is of low power and each subsequent pulse train is of consecutively higher power than the previous pulse train.

30. A method according to claim 26 wherein the backscatter intensity from said microbubbles from the first low power signal is recorded as a baseline value.

31. A method according to claim 30 wherein the backscatter intensity from the third high power signal is subtracted from said baseline to yield a difference value.

32. A method according to claim 31 wherein the difference value is compared to experimental reference values to measure ambient fluid pressure.

33. A method according to claim 31 wherein the ambient fluid pressure measurement is repeated and results are displayed on the screen of an ultrasound scanner associated with the defined region of interest.

34. A method according to claim 26 wherein the second high power signal is at a power level above the fragility threshold of one or more populations of said composition.

35. A method of determining the fragility thresholds of a plurality of populations of microbubbles and correlating said thresholds to ambient pressures at rupture surrounding said microbubbles comprising the steps of:
   a) determining the fragility slope of each said population from respective curves, said curves determined by measuring acoustic density as each of said population as it is acoustically interrogated along a channel versus distance along said channel;
   b) determining fragility curves by plotting each of said fragility slopes versus mechanical index, a measure of the acoustic power used to interrogate each said population;
   c) identifying the intercept of substantially linear portions of each of said fragility curves at zero fragility slope as the mechanical index at the threshold fragility for each said population;
   d) correlating each of said mechanical indices at the threshold fragility to an ambient pressure from a predetermined mechanical index-to-pressure relationship.

36. The method according to claim 35 wherein said fragility slopes are determined for a plurality of populations of microbubbles having differing wall thickness.

37. The method according to claim 35 wherein said fragility slopes are determined for a plurality of populations of microbubbles having differing moduli of elasticity.

38. The method according to claim 35 wherein said fragility slopes are determined for a plurality of populations of microbubbles having materials of differing molecular weight.

39. The method according to claim 35 wherein said fragility slopes are determined for a plurality of populations of microbubbles having materials of differing hoop strength.

40. The method according to claim 35 wherein said fragility curves are determined for a plurality of populations of microbubbles having differing wall thickness.

41. The method according to claim 35 wherein said fragility curves are determined for a plurality of populations of microbubbles having differing moduli of elasticity.

42. The method according to claim 35 wherein said fragility curves are determined for a plurality of populations of microbubbles having materials of differing molecular weight.

43. The method according to claim 35 wherein said fragility curves are determined for a plurality of populations of microbubbles having materials of differing hoop strength.

* * * * *